United States Patent [19]
Gericke et al.

[11] Patent Number: 5,744,641
[45] Date of Patent: Apr. 28, 1998

[54] SULFONYL- OR SULFINYLBENZOYLGUANIDINE DERIVATIVES

[75] Inventors: Rolf Gericke, Seeheim; Manfred Baumgarth, Darmstadt; Klaus-Otto Minck, Ober-Ramstadt; Norbert Beier, Reinheim, all of Germany

[73] Assignee: Merck Patent Gesellschaft mit beschränkter Haftung, Darmstadt, Germany

[21] Appl. No.: 699,053

[22] Filed: Aug. 9, 1996

[30] Foreign Application Priority Data

Aug. 11, 1995 [DE] Germany .................. 195 29 612.5

[51] Int. Cl.[6] .................. C07C 281/14; C07C 321/28
[52] U.S. Cl. .................. 564/228; 564/85; 564/88
[58] Field of Search .................. 562/162

[56] References Cited

U.S. PATENT DOCUMENTS

| | | | |
|---|---|---|---|
| 5,091,394 | 2/1992 | Englert et al. | 514/331 |
| 5,292,755 | 3/1994 | Englert et al. | 514/331 |

FOREIGN PATENT DOCUMENTS

| | | |
|---|---|---|
| 2106613 | 3/1994 | Canada . |
| 2112194 | 6/1994 | Canada . |
| 699663 | 8/1995 | European Pat. Off. . |

OTHER PUBLICATIONS

Noiri et al., "Cyclic RGE peptides ameliorate ischemic acute renal failure in rats," *Kidney International*, vol. 46, No. 4, Oct. '94, pp. 1050–1058.

Magazine et al., Evaluation of the Endothelin Receptor Populations Uisn Endothelin–1 Biotinylated at Lysine–9 Sidechain, Biochem. and Biophy. Res. Comm., vol. 181, No. 3, 1991, pp. 1245–1250.

*Primary Examiner*—Johann Richter
*Assistant Examiner*—Ebenezer Sackey
*Attorney, Agent, or Firm*—Millen, White, Zelano, & Branigan, P.C.

[57] ABSTRACT

4-Sulfonyl- or 4-sulfinylbenzoylguanidines of the formula I

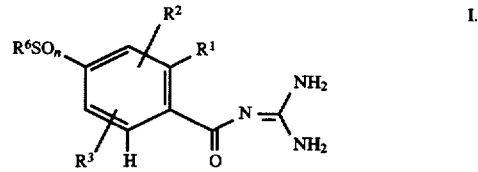

in which $R^1$, $R^2$, $R^3$, $R^6$ and n have the meanings indicated, and their physiologically acceptable salts exhibit antiarrhythmic properties and, act as inhibitors of the cellular $Na^+/H^+$ antiporter.

20 Claims, No Drawings

SULFONYL- OR SULFINYLBENZOYLGUANIDINE DERIVATIVES

BACKGROUND OF THE INVENTION

The invention relates to ortho-substituted 4-sulfonyl- or 4-sulfinylbenzoylguanidine derivatives of the formula I $$R^6SO_n \diagup\!\!\diagdown \diagup\!\!\diagdown R^1, R^2, R^3, H, C(=O)-N(H)-C(NH_2)=NH_2 \quad \text{I}$$

in which

R$^1$ is A, CF$_3$, CH$_2$F, CHF$_2$, C$_2$F$_5$, CN, NO$_2$ or Hal,

R$^2$ is —SO$_n$—R$^6$, —SO$_2$NR$^4$R$^5$, NO$_2$ or CF$_3$,

R$^3$ is H, Hal, A, OH, OA, CN, NO$_2$, CF$_3$, CH$_2$F, CHF2, C$_2$F$_5$ or CH$_2$CF$_3$,

R$^4$ and R$^5$ in each case independently of one another are H, A, cycloalkyl having 5 to 7 C atoms, cycloalkylmethyl having 4 to 8 C atoms, Ph or —CH$_2$-Ph, or else R$^4$ and R$^5$ together are also alkylene having 4 to 5 C atoms, it also being possible for a CH$_2$ group to be replaced by CO, O, S, NH, N—A or N—CH$_2$-Ph, R$^6$ is A, Ph, Het or C$_3$-C$_7$-cycloalkyl, Het is a mono- or binuclear saturated, unsaturated or aromatic heterocycle having 1 to 4 N, O and/or S atoms, bonded via N or C, which can be unsubstituted or mono-, di- or trisubstituted by Hal, SH, SA, NH$_2$, NHA, NA$_2$, CF$_3$, A, OH, OA, CN, NO$_2$, NHA, NA$_2$ and/or carbonyl oxygen, A is alkyl having 1 to 6 C atoms, Hal is F, Cl, Br or I, Ph is phenyl which is unsubstituted or mono-, di- or trisubstituted by A, OA, NR$^4$R$^5$, F, Cl, Br, I or CF$_3$ and n is 1 or 2, and their physiologically acceptable salts.

The invention was based on the object of finding novel compounds having useful properties, in particular those which can be used for the production of medicaments.

Upon further study of the specification and appended claims, further objects and advantages of this invention will become apparent to those skilled in the art.

It has been found that the compounds of the formula I and their physiologically acceptable salts have useful pharmacological properties together with good tolerability.

SUMMARY OF THE INVENTION

The novel compounds are inhibitors of the cellular Na$^+$/H$^+$ antiporter compounds, i.e. active compounds which inhibit the Na$^+$/H$^+$ exchange mechanism of the cells (Düsing et al., Med. Klin. 87, 378–384 (1992)) and which are thus good antiarrhythmics which are particularly suitable for the treatment of arrhythmias which occur as a result of oxygen deficiency.

The best known active compound of the acylguanidines groups is amiloride. This substance, however, primarily exhibits a hypotensive and saluretic action which, in particular in the treatment of cardiac arrhythmias, is undesirable, while the antiarrhythmic properties are only very weakly pronounced.

Moreover, structurally similar compounds are known, for example from EP 04 16 499.

The invention relates to compounds of the formula I and their physiologically acceptable salts.

The substances according to the invention of the present application exhibit a good cardioprotective action and are therefore particularly suitable for infarct treatment, infarct prophlaxis and for the treatment of angina pectoris. The substances are furthermore effective against all pathological hypoxic and ischaemic damage, so that the primary or secondary illnesses caused thereby can be treated. The active compounds are also highly suitable for preventive applications.

Due to the protective effects of these substances in pathological hypoxic or ischaemic situations, further application, include use in surgical interventions for the protection of temporarily undersupplied organs, in organ Transplantations for the protection of the removed organs, in angioplastic vascular or cardiac interventions, in ischaemias of the nervous system, in the therapy of states of shock and for the prevention of essential hypertension.

The compounds can furthermore also be employed as therapeutics in disorders caused by cell proliferation, such as arteriosclerosis, diabetic late complications, carcinomatous disorders, fibrotic disorders, in particular of the lungs, liver and kidneys, and organ hypertrophies and hyperplasias. The substances are moreover suitable for diagnostic use for the recognition of illnesses which are accompanied by an increased activity of the Na$^+$/H$^+$ antiporter, e.g., in erythrocytes, platelets or leucocytes.

The effects of the compounds can be determined with the aid of methods known per se, such as are indicated, for example, by N. Escobales and J. Figueroa in J. Membrane Biol. 120, 41–49 (1991) or by L. Counillon, W. Scholz, H. J. Lang and J. Pouysségur in Mol. Pharmacol. 44, 1041–1045 (1993).

Suitable experimental animals are, for example, mice, rats, guinea pigs, dogs, cats, monkeys or pigs.

The compounds can therefore be used in human and veterinary medicine as pharmaceutically active compounds. They can furthermore be used as intermediates for the preparation of further pharmaceutically active compounds.

In the formulae indicated, A is a branched or unbranched alkyl group having 1–6, preferably 1–4, in particular 1, 2 or 3 C atoms, specifically preferably methyl, furthermore preferably ethyl, propyl, isopropyl, butyl, isobutyl, additionally preferably sec-butyl, tert-butyl, pentyl, isopentyl (3-methylbutyl), hexyl or isohexyl (4-methylpentyl).

R$^1$ is preferably A, in particular methyl or ethyl, CF$_3$ or Hal, in particular F or Cl. Furthermore, however, preferably also CH$_2$F, CHF$_2$ or C$_2$F$_5$. R$^1$ is particularly preferably methyl or ethyl.

R$^2$ is preferably A—SO$_2$, NO$_2$ or CF$_3$. R$^2$ is particularly preferably H$_3$C—SO$_2$—.

R$^3$ is preferably H, but also A, CF$_3$, Cl, Br, F, CN, OA and NO$_2$. One of the two radicals R$^2$ and R$^3$ is preferably in the 3- or 5-position of the benzoyl group. If one of the radicals is A—SO$_2$—, this is preferably located in the meta-position relative to the benzoylguanidine group.

R$^4$, as well as R$^5$, are preferably H or A.

If R$^4$ and R$^5$ together are alkylene, the alkylene group is preferably unbranched, specifically preferably —(CH$_2$)$_k$—, k being 4 or 5; but also preferably —(CH$_2$)$_2$—O—(CH$_2$)$_2$—, —(CH$_2$)$_2$—NH—(CH$_2$)$_2$—, —(CH$_2$)$_2$—NA—(CH$_2$)$_2$—, —CH$_2$—O—(CH$_2$)$_2$, —CH$_2$—NH—(CH$_2$)$_2$— or —CH$_2$—NA—(CH$_2$)$_2$— and —CO—(CH$_2$)$_3$—, —CO—(CH$_2$)$_4$— or —CH$_2$—CO—(CH$_2$)$_2$—.

Ph is preferably phenyl which is unsubstituted or monosubstituted by Cl, F, A, OA, NH$_2$, NHA, NA$_2$ or CF$_3$.

R$^6$ is preferably A, or else preferably also unsubstituted phenyl, or phenyl which is monosubstituted by A, Hal or CF$_3$, furthermore also preferably cycloalkyl having 5–7 C atoms. R$^6$ is preferably C$_1$ to C$_6$-alkyl or C$_3$ to C$_7$-cycloalkyl. If R$^6$ is acyclic, the radical is preferably one of the alkyl radicals which are also preferred for A. Particularly preferred cycloalkyl radicals which R$^6$ can be are cyclopropyl, cyclopentyl, cyclohexyl or their derivatives monosubstituted by A, in particular methyl, ethyl or isopropyl.

The variable n is 1 or 2.

Hal is preferably F, Cl or Br.

Her is preferably 2- or 3-furyl, 2- or 3-thienyl, 1-, 2- or 3-pyrrolyl, 1-, 2-, 4-, or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4-, or 5-isothiazolyl, 2-, 3- or 4-pyridyl, 2-, 4-, 5- or 6-pyrimidinyl, additionally preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals can also be partially or completely hydrogenated. Het can thus also be, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2-, or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or 8-isoquinolinyl.

In general, all radicals such as, for example, Het or Ph, which occur several times, can be identical or different, i.e., are independent of one another.

The invention accordingly relates in particular to those compounds of the formula I in which at least one of the radicals mentioned has one of the preferred meanings indicated above. Some preferred groups of compounds can be expressed by the formulae Ia to Ih below, which correspond to the formula I and in which the radicals not described in greater detail have the meaning indicated in the formula I, but in which in Ia R$^1$ is A and R$^2$ is —SO$_2$—A or NO$_2$;

in Ib R$^1$ is A and R$^6$ is branched or unbranched alkyl having 1 to 6 C atoms;

in Ic R$^1$ is A and R$^6$ is cycloalkyl having 5 to 7 C atoms;

in Id R$^6$ is branched or unbranched alkyl having 1–6 C atoms, R$^2$ is —SO$_2$—A, CF$_3$ or NO$_2$ and R$^1$ is methyl or ethyl;

in Ie R$^6$ is methyl, ethyl, propyl, isopropyl, butyl, cycloalkyl having 3 to 7 C atoms, or phenyl which is unsubstituted or monosubstituted by Cl, Br, methyl or CF$_3$, and R$^2$ is in the meta-position relative to the amide group and is —SO$_2$—A;

in If R$^1$ and R$^2$ are in the para-position to one another and R$^1$ is A and R$^2$ is —SO$_2$—A;

in Ig R$^6$ is phenyl or methyl, n=2, R$^1$ is methyl or ethyl and R$^2$ is in the meta-position relative to the amide group and is —SO$_2$—A;

in Ih R$^1$ is methyl or ethyl, R$^2$ is SO$_2$—CH$_3$ and R$^6$ is methyl, ethyl, propyl, isopropyl, phenyl, cyclopentyl or cyclohexyl.

All compounds mentioned in Ia-Ih in which, at the same time, n=2 are furthermore particularly preferred.

The invention furthermore relates to a process for the preparation of the compounds of the formula I according to claim 1, and of their salts, characterized in that a compound of the formula II

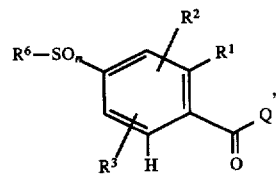

in which R$^1$, R$^2$, R$^3$, R$^6$ and n have the meanings indicated before and Q is Cl, Br, OA, O-CO-A, O-CO-Ph, OH or another reactive esterified OH group or readily nucleophilically substitutable leaving group, is reacted with guanidine, or in that a benzoylguanidine of the formula III

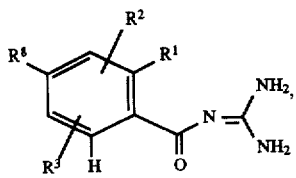

in which

R$^1$, R$^2$ and R$^3$ have the meanings indicated before, and

R$^8$ is F, Cl, Br, I or H, is reacted with a compound of the formula IV

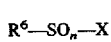   IV in which

R$^6$ has the indicated meaning and

X is H, Cl, Br or I.

in the presence of a catalyst, after prior metallation or transmetallation, or in that a benzoylguanidine of the formula V

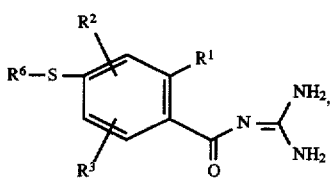

is reacted with a suitable oxidizing agent, or in that a compound otherwise corresponding to the formula I, but which instead of one or more hydrogen atoms contains one or more reducible groups and/or one or more additional C—C and/or C—N bonds, is treated with a reducing agent, or in that a compound otherwise corresponding to the formula I, but which instead of one or more hydrogen atoms contains one or more solvolyzable groups, is treated with a solvolyzing agent and/or in that a base of the formula I obtained is converted into one of its salts by treating with an acid.

The compounds of the formula I are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart; Organic Reactions, John Wiley & Sons, Inc., New York; and in the patent application indicated above), namely under reaction conditions which are known and are suitable for the reactions mentioned. In this case use can also be made of variants which are known per se but not mentioned here in greater detail.

If desired, the starting substances can also be formed in situ in such a way that they are not isolated from the reaction mixture, but are immediately reacted further to give the compounds of the formula I.

Compounds of the formula t are preferably prepared by reacting an activated carboxylic acid derivative of the formula II, where Q is particularly preferably Cl or —O—CH$_3$, with guanidine. Reaction variants are also particularly suitable in which the free carboxylic acid II (Q=OH) is reacted in a manner known per se to give the respective activated derivative and this is then reacted directly, without intermediate isolation, with guanidine. Methods in which intermediate isolation is unnecessary are, for example, activation with carbonyldiimidazole, dicyclohexylcarbodiimide or the Mukayama variant (Angew. Chem. 91, 788–812 (1979).

The carboxylic acids and carboxylic acid derivatives of the formula II are generally known. They are prepared, in particular, from the corresponding halogen compounds by nucleophilic aromatic substitution. The exchange H 1→SR$^6$ is preferably carried out at the acid stage. Reaction is then carried out with an oxidizing agent such as H$_2$O$_2$, peracetic acid, perbenzoic acid or sodium perborate.

The carboxylic acids of the formula II or their derivatives are furthermore prepared by metallating suitable benzoic acid derivatives of the formula VI

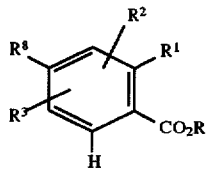

in which R$^1$, R$^2$, R$^3$ and R$^8$ have the meanings indicated and R is hydrogen or A, and then reacting with an alkylsulfonyl derivative of the formula IV. A suitable base for the metallation is, for example, lithium diisopropylamide.

In the cross-couplings mentioned before, a carboxylic acid or an ester derivative of the formula VI in which R$^8$ is Cl, Br or I is reacted with an organometallic alkyl compound, which is prepared in situ from a compound of the formula IV by metallation with a metallating reagent known per se, in the presence of a suitable metal catalyst, in particular one of those mentioned before.

The reaction is carried out in analogy to the reaction of the compounds III and IV. It is described below.

The reaction of a reactive carboxylic acid derivative of the formula II with guanidine is carried out in a manner known per se, preferably in a protic or aprotic polar or non-polar inert organic solvent.

Suitable solvents are mentioned below for the reaction of the compounds III and IV. Particularly preferred solvents, however, are methanol, THF, dimethoxyethane, dioxane or mixtures which can be prepared therefrom, as well as water. Suitable reaction temperatures are, for example, temperatures between 20° and the boiling point of the solvent. The reaction times are between 5 min and 12 h. It is expedient to employ an acid scavenger in the reaction. All types of bases which do not interfere in the reaction itself are suitable for this purpose. The use of inorganic bases such as potassium carbonate or of organic bases such as triethylamine or pyridine or else an excess of guanidine, however, is particularly suitable.

Compounds of the formula I according to claim 1 can furthermore be prepared by reacting a benzoylguanidine of the formula III with a compound of the formula IV. The starting substances of the formula III can be prepared in a simple manner by reaction of appropriately substituted benzoic acids or reactive acid derivatives which can be derived therefrom, such as, for example, acid halides, esters or anhydrides, with guanidine, under reaction conditions such as are known per se and generally customary for amide preparation. In turn, those reaction variants are particularly suitable such as have been indicated before for the reaction of compound II with guanidine.

The compounds of the formula IV, like the methods for their preparation, are known per se. If they are not known, they can be prepared by the methods known per se.

The preparation of the compound II and the reaction of the compound III with a compound of the formula IV is carried out in a manner known per se, preferably in a protic or aprotic polar inert organic solvent.

In the preparation of II or in the reaction of III with IV, it is likewise expedient to work in the presence of a base or with an excess of the basic component. Suitable bases are preferably, for example, alkali metal or alkaline earth metal hydroxides, carbonates, alcoholates or organic bases such as triethylamine or pyridine, which are also used in an excess and can then simultaneously serve as a solvent.

Suitable inert solvents are, in particular, alcohols such as methanol, ethanol, isopropanol, n-butanol or tert-butanol; ethers such as diethyl ether, diisopropyl ether, tetrahydrofuran (THF) or dioxane; glycol ethers such as ethylene glycol monomethyl or monoethyl ether (methylglycol or ethylglycol), ethylene glycol dimethyl ether (diglyme); ketones such as acetone or butanone; nitriles such as acetonitrile; nitro compounds such as nitromethane or nitrobenzene; esters such as ethyl acetate; amides such as hexamethylphosphoramide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Mixtures of these solvents with one another are additionally suitable.

A particularly preferred procedure when reacting III with IV consists in suspending the corresponding benzoylguanidine in an inert solvent, such as, for example, toluene, treating with a Pd(II) catalyst and then adding dropwise the desired previously transmetallated compound, e.g. a Zn-alkylsulfonyl compound, of the formula IV.

A further preferred variant for the preparation of compounds of the formula I consists in oxidizing a compound of the formula V to a sulfonyl compound using an oxidizing agent. Suitable oxidizing agents are, for example, hydrogen peroxide, peracetic acid, perbenzoic acid or sodium perborate. The compounds of the formula V can be prepared, for example, from the corresponding halogen compounds by nucleophilic aromatic substitution, the halogen/$SR^6$ exchange preferably taking place at the acid stage and a conversion into the benzoylguanidine then being performed.

The sulfinylbenzoylguanidines of the formula I (n=1) exist in racemic form and can be resolved into enantiomers. These compounds are included by the invention both as racemates, but also in enantiomerically pure form.

The compounds of the formula I can furthermore be obtained by setting them free from their functional derivatives by solvolyis, in particular hydrolysis, or by hydrogenolysis.

Preferred starting substances for solvolysis or hydrogenolysis are those which otherwise correspond to the formula I, but instead of one or more free amino and/or hydroxy groups contain corresponding protected amino and/or hydroxy groups, preferably those which instead of an H atom which is linked to an N atom carry an amino protective group, in particular those which instead of an HN group carry an R'-N group in which R' is an amino protective group, and/or those which instead of the H atom of a hydroxy group carry a hydroxy protective group, e.g., those which correspond to the formula I, but instead of an OH group carry an OR" group, in which R" is a hydroxy protective group.

Two or more—identical or different—protective amino and/or hydroxy groups can also be present in the molecule of the starting substance. If the protective groups present differ from one another, in many cases they can be removed selectively.

The expression "amino protective group" is generally known and relates to groups which are suitable for protecting (for blocking) an amino group from chemical reactions, but which are easily removable after the desired chemical reaction has been carried out at another position in the molecule. Typical groups of this type are, in particular, unsubstituted or substituted acyl, aryl (e.g. 2,4-dinitrophenyl (DNP)), aralkoxymethyl (e.g. benzyloxymethyl (BOM)) or aralkyl groups (e.g. benzyl, 4-nitrobenzyl, triphenylmethyl). As the amino protective groups are removed after the desired reaction (or reaction sequence), their nature and size is otherwise not critical; however, those having 1–20, in particular 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and also, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or tolyl; aryloxyalkanoyl such as phenoxyacetyl; alkoxycarbonyl such as methoxycarbonyl, ethoxycarbonyl, 2,2,2-trichloroethoxycarbonyl, isopropoxycarbonyl, tert-butoxycarbonyl (BOC), 2-iodo-ethoxycarbonyl; aralkyloxycarbonyl such as benzyloxycarbonyl (CBZ), 4-methoxybenzyloxycarbonyl, 9-fluorenylmethoxycarbonyl (FMOC). Preferred amino protective groups are BOC, DNP and BOM, furthermore CBZ, benzyl and acetyl.

The expression "hydroxy protective group" is likewise generally known and relates to groups which are suitable for protecting a hydroxy group from chemical reactions, but which are easily removable after the desired chemical reaction has been carried out at another position in the molecule. Typical of groups of this type are the abovementioned unsubstituted or substituted aryl, aralkyl or acyl groups, furthermore also alkyl groups. The nature and size of the hydroxy protective groups is not critical, as they are removed again after the desired chemical reaction or reaction sequence; groups having 1–20, in particular 1–10, C atoms are preferred. Examples of hydroxy protective groups are, inter alia, tert-butyl, benzyl, p-nitrobenzoyl, p-toluenesulfonyl and acetyl, benzyl and acetyl being particularly preferred.

The functional derivatives of the compounds of the formula I to be used as starting substances can be prepared by customary methods, such as are described, for example, in the standard works and patent applications mentioned, e.g., by reaction of compounds which correspond to the formulae ii and III, but where at least one of these compounds contains a protective group instead of an H atom.

The liberation of the compounds of the formula I from their functional derivatives is carried out—depending on the protective group used—e.g., with strong acids, expediently with trifluoroacetic acid or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible, but not always necessary.

Suitable inert solvents are preferably organic, for example carboxylic acids such as acetic acid, ethers such as tetrahydrofuran (THF) or dioxane, amides such as dimethylformamide (DMF), halogenated hydrocarbons such as dichloromethane, furthermore also alcohols such as methanol, ethanol or isopropanol and also water. Mixtures of the abovementioned solvents are furthermore possible- Trifluoroacetic acid is preferably used in an excess without addition of a further solvent, perchloric acid in the form of a mixture of acetic acid and 70% perchloric acid in the ratio 9:1. The reaction temperatures for the cleavage are expediently between approximately 0 and approximately 50°; the reaction is preferably carried out between 15° and 30° (room temperature).

The BOC group can be removed, for example, preferably using 40% trifluoroacetic acid in dichloromethane or using approximately 3 to 5 N HCl in dioxane at 15°–60°, the FMOC group using an approximately 5°–20% solution of dimethylamine, diethylamine or piperidine in DMF at 15°–50°. Removal of the DNP group is also carried out, for example, using an approximately 3–10% solution of 2-mercaptoethanol in DMF/water at 15°–30°.

Hydrogenolytically removable protective groups (e.g., BOM, CBZ or benzyl) can be removed, for example, by treatment with hydrogen in the presence of a catalyst (e.g., of a noble metal catalyst such as palladium, expediently on a support such as carbon). Suitable solvents in this case are those indicated above, in particular, for example, alcohols such as methanol or ethanol or amides such as DMF. The hydrogenolysis is generally carried out at temperatures between approximately 0° and 100° and pressures between approximately 1 and 200 bar, preferably at 20°–30° and 1–10 bar. Hydrogenolysis of the CBZ group is readily carried out, for example, on 5–10% Pd-C in methanol at 20°–30°

A base of the formula I can furthermore be converted into the associated acid addition salt using an acid. Possible acids for this reaction are those which yield physiologically acceptable salts. Inorganic acids can thus be used, e.g., sulfuric acid, nitric acid, hydrohalic acids such as hydrochloric acid or hydrobromic acid, phosphoric acids such as orthophosphoric acid, sulfonic acid, furthermore organic acids, in particular aliphatic, alicyclic, araliphatic, aromatic or heterocyclic mono- or polybasic carboxylic, sulfonic or sulfuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid.

The compounds of the formula I and their physiologically acceptable salts can be used for the production of pharmaceutical preparations, in particular by a non-chemical route. In this context, they can be brought into a suitable dose form together with at least one solid, liquid and/or semi-liquid excipient or auxiliary and, if appropriate, in combination with one or more further active compounds.

The invention furthermore relates to compositions, particular pharmaceutical preparations, comprising at least one compound of the formula I and/or one of its physiologically acceptable salts.

These preparations can be used as medicaments in human or veterinary medicine. Possible excipients are organic or inorganic substances which are suitable for enteral (e.g., oral), parenteral or topical application and do not react with the novel compounds, for example water, vegetable oils, benzylalcohols, polyethylene glycols, glycerol triacetate, gelatin, carbohydrates such as lactose or starch, magnesium stearate, talc, lanolin and petroleum jelly. Tablets, coated tablets, capsules, syrups, juices or drops are used, in particular, for oral administration, suppositories are used for rectal administration, solutions, preferably oily or aqueous solutions, furthermore suspensions, emulsions or implants, are used for parenteral administration, and ointments, creams, pastes, lotions, gels, sprays, foams, aerosols, solutions (e.g.,solutions in alcohol such as ethanol or isopropanol, acetonitrile, DMF, dimethylacetamide, 1,2-propanediol or mixtures thereof with one another and/or with water) or powders are used for topical application. The novel compounds can also be lyophilized and the lyophilisates obtained can be used, for example, for the production of injection preparations.

Liposomal preparations are suitable, in particular for topical application. The preparations indicated can be sterilized and/or contain auxiliaries such as glidants, preservatives, stabilizers and/or wetting agents, emulsifiers, salts for effecting the osmotic pressure, buffer substances, colorants, flavoring and/or aromatic substances. If desired, they can also contain one or more further active compounds, e.g.,one or more vitamins.

The compounds of the formula I and their physiologically acceptable salts can be administered to humans or animals, in particular mammals such as monkeys, dogs, cats, rats or mice, and used in the therapeutic treatment of the human or animal body and also in the control of illnesses, in particular in the therapy and/or prophylaxis of disorders of the cardiovascular system. They are therefore suitable for the treatment of arrhythmias, in particular if these are caused by oxygen deficiency, of angina pectoris, infarcts, ischaemias of the nervous system such as, for example, stroke or cerebral edema, of states of shock and for preventive treatment.

The substances can furthermore be employed as therapeutics in disorders in which cell proliferation plays a part, such as arteriosclerosis, diabetic late complications, carcinomatous disorders, fibroses and organ hypertrophies and hyperplasias, in particular in disorders of the prostate.

In this case the substances according to the invention are generally administered in analogy to known antiarrhythmics, e.g., aprindine, preferably in dosages of between approximately 0.01 and 5 mg, in particular of between 0.02 and 0.5 mg per dose unit. The daily dose is preferably between approximately 0.0001 and 0.1, in particular between 0.0003 and 0.01 mg/kg, of body weight. The specific dose for each specific patient can be routinely determined, and depends on a variety of factors, for example on the efficacy of the specific compound employed, on age, body weight, general state of health, sex, on the diet, on the time and route of administration, on the excretion rate, pharmaceutical substance combination and severity of the particular disorder to which the therapy relates. Oral administration is preferred.

In the following Examples, "customary working up" means:

If necessary, water is added, the mixture is acidified and extracted or washed with an organic solvent such as ethyl acetate, the organic phase is separated off, dried over sodium sulfate, filtered and 0 evaporated, and the residue is purified by chromatography and/or crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 195 29 612.5, filed Aug. 11, 1995, are hereby incorporated by reference.

EXAMPLES

Example 1

900 mg of Na are dissolved in 30 ml of methanol, 3 g of guanidium chloride are added, and the mixture is stirred at room temperature for 30 minutes and filtered. After removing the solvent and washing with toluene, the residue is taken up in 30 ml of ethylene glycol monomethyl ether and added to a solution of 1 g of 2-methyl-4,5-di (methylsulfonyl)-benzoyl chloride [obtainable by reaction of 2-methyl-4-chloro-5-methylsulfonylbenzoic acid with Na methylthiolate, subsequent oxidation with Na perborate, conversion into the acid chloride, e.g. with $SOCl_2$] in 40 ml of ethylene glycol monomethyl ether. The mixture is stirred at room temperature for 2 hours and diluted with 100 ml of ice-water, and 10 ml of 1N HCl solution are added. The mixture is then washed twice, in each case using 50 ml of ethyl acetate, and adjusted to a pH of 9. After customary working up and removal of the solvent, N-diaminomethylene-2-methyl-4,5-di(methylsulfonyl) benzamide, m.p. 238°–240°, is obtained after recrystallizing from diethyl ether.

The following are obtained analogously by reaction of guanidine with 2-methyl-4-phenylsulfonyl-5-methylsulfonylbenzoyl chloride N-diaminomethylene-2-methyl-4-phenylsulfonyl-5-methylsulfonylbenzamide, m.p. 235°–237°;
with 2-methyl-4-propylsulfonyl-5-methylsulfonylbenzoyl chloride N-diaminomethylene-2-methyl-4-propylsulfonyl-5-methylsulfonylbenzamide;
with 2-methyl-4-butylsulfonyl-5-methylsulfonylbenzoyl chloride N-diaminomethylene-2-methyl-4-butylsulfonyl-5-methylsulfonylbenzamide;
with 2-methyl-4-(2-butylsulfonyl)-5-methylsulfonylbenzoyl chloride N-diaminomethylene-2-methyl-4-(2-butylsulfonyl)-5-methylsulfonylbenzamide;
with 2-methyl-4-pentylsulfonyl-5-methylsulfonylbenzoyl chloride N-diaminomethylene-2-methyl-4-pentylsulfonyl-5-methylsulfonylbenzamide;
with 2-methyl-4-(2-pentylsulfonyl)-5-methylsulfonylbenzoyl chloride N-diaminomethylene-2-methyl-4-(2-pentylsulfonyl)-5-methylsulfonylbenzamide;
with 2-methyl-4-(3-pentylsulfonyl)-5-methylsulfonylbenzoyl chloride N-diaminomethylene-2-methyl-4-(3-pentylsulfonyl)-5-methylsulfonylbenzamide;
with 2-methyl-4-tert-butylsulfonyl-5-methylsulfonylbenzoyl chloride N-diaminomethylene-2-methyl-4-tert-butylsulfonyl-5-methylsulfonylbenzamide;
with 2-methyl-4-isopropylsulfonyl-5-methylsulfonylbenzoyl chloride N-diaminomethylene-2-methyl-4-isopropylsulfonyl-5-methylsulfonylbenzamide;
with 2-methyl-4-hexylsulfonyl-5-methylsulfonylbenzoyl chloride, N-diaminomethylene-2-methyl-4-hexylsulfonyl-5-methylsulfonylbenzamide;
with 2-methyl-4-cyclopropylsulfonyl-5-methylsulfonylbenzoyl chloride N-diaminomethylene-2-methyl-4-cyclopropylsulfonyl-5-methylsulfonylbenzamide;
with 2-methyl-4-cyclopentylsulfonyl-5-methylsulfonylbenzoyl chloride N-diaminomethylene-2-methyl-4-cyclopentylsulfonyl-5-methylsulfonylbenzamide;
with 2-methyl-4-cyclohexylsulfonyl-5-methylsulfonylbenzoyl chloride N-diaminomethylene-2-methyl-4-cyclohexylsulfonyl-5-methylsulfonylbenzamide;
with 2-methyl-4-(2-methylcyclopentylsulfonyl)-5-methylsulfonylbenzoyl chloride N-diaminomethylene-2-methyl-4-(2-methylcyclopentylsulfonyl)-5-methylsulfonylbenzamide;
with 2-methyl-4-cyclobutylsulfonyl-5-methylsulfonylbenzoyl chloride N-diaminomethylene-2-methyl-4-cyclobutylsulfonyl-5-methylsulfonylbenzamide;
with 2-methyl-4-cycloheptylsulfonyl-5-methylsulfonylbenzoyl chloride N-diaminomethylene-2-methyl-4-cycloheptylsulfonyl-5-methylsulfonylbenzamide;
with 2-ethyl-4-phenylsulfonyl-5-methylsulfonylbenzoyl chloride N-diaminomethylene-2-ethyl-4-phenylsulfonyl-5-methylsulfonylbenzamide;
with 2-ethyl-4,5-di-(methylsulfonyl)benzoyl chloride N-diaminomethylene-2-ethyl-4,5-di-(methylsulfonylbenzamide;
with 2-ethyl-4-ethylsulfonyl-5-methylsulfonyl-benzoyl chloride N-diaminomethylene-2-ethyl-4-ethylsulfonyl-5-methylsulfonylbenzamide;
with 2-ethyl-4-propylsulfonyl-5-methylsulfonylbenzoyl chloride N-diaminomethylene-2-ethyl-4-propylsulfonyl-5-methylsulfonylbenzamide;
with 2-ethyl-4-butylsulfonyl-5-methylsulfonylbenzoyl chloride N-diaminomethylene-2-ethyl-4-butylsulfonyl-5-methylsulfonylbenzamide;
with 2-ethyl-4-(2-butylsulfonyl)-5-methylsulfonylbenzoyl chloride N-diaminomethylene-2-ethyl-4-(2-butylsulfonyl)-5-methylsulfonylbenzamide;
with 2-ethyl-4-pentylsulfonyl-5-methylsulfonylbenzoyl chloride N-diaminomethylene-2-ethyl-4-pentylsulfonyl-5-methylsulfonylbenzamide;
with 2-ethyl-4-(2-pentylsulfonyl)-5-methylsulfonylbenzoyl chloride N-diaminomethylene-2-ethyl-4-(2-pentylsulfonyl)-5-methylsulfonylbenzamide;
with 2-ethyl-4-(3-pentylsulfonyl)-5-methylsulfonylbenzoyl chloride N-diaminomethylene-2-ethyl-4-(3-pentylsulfonyl)-5-methylsulfonylbenzamide;
with 2-ethyl-4-tert-butylsulfonyl-5-methylsulfonylbenzoyl chloride N-diaminomethylene-2-ethyl-4-tert-butylsulfonyl-5-methylsulfonylbenzamide;
with 2-ethyl-4-isopropylsulfonyl-5-methylsulfonylbenzoyl chloride N-diaminomethylene-2-ethyl-4-isopropylsulfonyl-5-methylsulfonylbenzamide;
with 2-ethyl-4-hexylsulfonyl-5-methylsulfonylbenzoyl chloride N-diaminomethylene-2-ethyl-4-hexylsulfonyl-5-methylsulfonylbenzamide;
with 2-ethyl-4-cyclopropylsulfonyl-5-methylsulfonylbenzoyl chloride N-diaminomethylene-2-ethyl-4-cyclopropylsulfonyl-5-methylsulfonylbenzamide;
with 2-ethyl-4-cyclopentylsulfonyl-5-methylsulfonylbenzoyl chloride N-diaminomethylene-2-ethyl-4-cyclopentylsulfonyl-5-methylsulfonylbenzamide;
with 2-ethyl-4-cyclohexylsulfonyl-5-methylsulfonylbenzoyl chloride N-diaminomethylene-2-ethyl-4-cyclohexylsulfonyl-5-methylsulfonylbenzamide;
with 2-ethyl-4-(2-methylcyclopentylsulfonyl)-5-methylsulfonylbenzoyl chloride N-diaminomethylene-2-ethyl-4-(2-methylcyclopentylsulfonyl)-5-methylsulfonylbenzamide;
with 2-ethyl-4-cyclobutylsulfonyl-5-methylsulfonylbenzoyl chloride N-diaminomethylene-2-ethyl-4-cyclobutylsulfonyl-5-methylsulfonylbenzamide;

with 2-ethyl-4-cycloheptylsulfonyl-5-methylsulfonylbenzoyl chloride

N-diaminomethylene-2-ethyl-4-cycloheptylsulfonyl-5-methylsulfonylbenzamide.

Example 2

Analogously to Example 1, by reaction of 1.8 g of 2-methyl-4-methylsulfonyl-5-nitrobenzoyl chloride [obtainable by reaction of methyl 2-methyl-4-bromo-5-nitrobenzoates with methylthiozinc chloride in the presence of Pd(II)-[1,1'-bis(diphenylphosphino)-ferrocene]chloride and CuI, subsequent oxidation with $H_2O_2$, hydrolysis and conversion into the acid chloride, e.g. with $SOCl_2$] with 1.5 g of guanidine in methanol N-diaminomethylene-2-methyl-4-(methylsulfonyl)-5-nitrobenzamide is obtained.

The following are obtained analogously by reaction of guanidine with 2-methyl-4-phenylsulfonyl-5-nitrobenzoyl chloride N-diaminomethylene-2-methyl-4-phenylsulfonyl-5-nitrobenzamide;

with 2-methyl-4-ethylsulfonyl-5-nitrobenzoyl chloride

N-diaminomethylene-2-methyl-4-ethylsulfonyl-5-nitrobenzamide;

with 2-methyl-4-propylsulfonyl-5-nitrobenzoyl chloride

N-diaminomethylene-2-methyl-4-propylsulfonyl-5-nitrobenzamide;

with 2-methyl-4-butylsulfonyl-5-nitrobenzoyl chloride

N-diaminomethylene-2-methyl-4-butylsulfonyl-5-nitrobenzamide;

with 2-methyl-4-(2-butylsulfonyl)-5-nitrobenzoyl chloride

N-diaminomethylene-2-methyl-4-(2-butylsulfonyl)-5-nitrobenzamide;

with 2-methyl-4-pentylsulfonyl-5-nitrobenzoyl chloride

N-diaminomethylene-2-methyl-4-pentylsulfonyl-5-nitrobenzamide;

with 2-methyl-4-(2-pentylsulfonyl)-5-nitrobenzoyl chloride

N-diaminomethylene-2-methyl-4-(2-pentylsulfonyl)-5-nitrobenzamide;

with 2-methyl-4-(3-pentylsulfonyl)-5-nitrobenzoyl chloride

N-diaminomethylene-2-methyl-4-(3-pentylsulfonyl)-5-nitrobenzamide;

with 2-methyl-4-tert-butylsulfonyl-5-nitrobenzoyl chloride

N-diaminomethylene-2-methyl-4-tert-butylsulfonyl-5-nitrobenzamide;

with 2-methyl-4-isopropylsulfonyl-5-nitrobenzoyl chloride

N-diaminomethylene-2-methyl-4-isopropylsulfonyl-5-nitrobenzamide;

with 2-methyl-4-hexylsulfonyl-5-nitrobenzoyl chloride

N-diaminomethylene-2-methyl-4-hexylsulfonyl-5-nitrobenzamide;

with 2-methyl-4-cyclopropylsulfonyl-5-nitrobenzoyl chloride

N-diaminomethylene-2-methyl-4-cyclopropylsulfonyl-5-nitrobenzamide;

with 2-methyl-4-cyclopentylsulfonyl-5-nitrobenzoyl chloride

N-diaminomethylene-2-methyl-4-cyclopentylsulfonyl-5-nitrobenzamide;

with 2-methyl-4-cyclohexylsulfonyl-5-nitrobenzoyl chloride

N-diaminomethylene-2-methyl-4-cyclohexylsulfonyl-5-nitrobenzamide;

with 2-methyl-4-(2-methylcyclopentylsulfonyl)-5-nitrobenzoyl chloride

N-diaminomethylene-2-methyl-4-(2-methylcyclopentylsulfonyl)-5-nitrobenzamide;

with 2-methyl-4-cyclobutylsulfonyl-5-nitrobenzoyl chloride

N-diaminomethylene-2-methyl-4-cyclobutylsulfonyl-5-nitrobenzamide;

with 2-methyl-4-cycloheptylsulfonyl-5-nitrobenzoyl chloride

N-diaminomethylene-2-methyl-4-cycloheptylsulfonyl-5-nitrobenzamide;

with 2-ethyl-4-phenylsulfonyl-5-nitrobenzoyl chloride

N-diaminomethylene-2-ethyl-4-phenylsulfonyl-5-nitrobenzamide;

with 2-ethyl-4,5-di-(methylsulfonyl)benzoyl chloride

N-diaminomethylene-2-ethyl-4-methylsulfonyl-5-nitrobenzamide;

with 2-ethyl-4-ethylsulfonyl-S-nitrobenzoyl chloride

N-diaminomethylene-2-ethyl-4-ethylsulfonyl-5-nitrobenzamide;

with 2-ethyl-4-propylsulfonyl-5-nitrobenzoyl chloride

N-diaminomethylene-2-ethyl-4-propylsulfonyl-5-nitrobenzamide;

with 2-ethyl-4-butylsulfonyl-5-nitrobenzoyl chloride

N-diaminomethylene-2-ethyl-4-butylsulfonyl-5-nitrobenzamide;

with 2-ethyl-4-(2-butylsulfonyl)-5-nitrobenzoyl chloride

N-diaminomethylene-2-ethyl-4-(2-butylsulfonyl)-5-nitrobenzamide;

with 2-ethyl-4-pentylsulfonyl-5-nitrobenzoyl chloride

N-diaminomethylene-2-ethyl-4-pentylsulfonyl-5-nitrobenzamide;

with 2-ethyl-4-(2-pentylsulfonyl)-5-nitrobenzoyl chloride

N-diaminomethylene-2-ethyl-4-(2-pentylsulfonyl)-5-nitrobenzamide;

with 2-ethyl-4-(3-pentylsulfonyl)-5-nitrobenzoyl chloride

N-diaminomethylene-2-ethyl-4-(3-pentylsulfonyl)-5-nitrobenzamide;

with 2-ethyl-4-tert-butylsulfonyl-5-nitrobenzoyl chloride

N-diaminomethylene-2-ethyl-4-tert-butylsulfonyl-5nitrobenzamide;

with 2-ethyl-4-isopropylsulfonyl-5-nitrobenzoyl chloride

N-diaminomethylene-2-ethyl-4-isopropylsulfonyl-5-nitrobenzamide;

with 2-ethyl-4-hexylsulfonyl-5-nitrobenzoyl chloride

N-diaminomethylene-2-ethyl-4-hexylsulfonyl-5-nitrobenzamide;

with 2-ethyl-4-cyclopropylsulfonyl-5-nitrobenzoyl chloride

N-diaminomethylene-2-ethyl-4-cyclopropylsulfonyl-5-nitrobenzamide;

with 2-ethyl-4-cyclopentylsulfonyl-5-nitrobenzoyl chloride

N-diaminomethylene-2-ethyl-4-cyclopentylsulfonyl-5-nitrobenzamide;

with 2-ethyl-4-cyclohexylsulfonyl-5-nitrobenzoyl chloride

N-diaminomethylene-2-ethyl-4-cyclohexylsulfonyl-5-nitrobenzamide;

with 2-ethyl-4-(2-methylcyclopentylsulfonyl)-5-nitrobenzoyl chloride

N-diaminomethylene-2-ethyl-4-(2-methylcyclopentylsulfonyl)-5-nitrobenzamide;

with 2-ethyl-4-cyclobutylsulfonyl-5-nitrobenzoyl chloride

N-diaminomethylene-2-ethyl-4-cyclobutylsulfonyl-5-nitrobenzamide;

with 2-ethyl-4-cycloheptylsulfonyl-5-nitrobenzoyl chloride

N-diaminomethylene-2-ethyl-4-cycloheptylsulfonyl-5-nitrobenzamide.

Example 3

Analogously to Example 1, by reaction of 1.8 g of 2-methyl-4-methylsulfonyl-5-trifluoromethylbenzoyl chloride [obtainable by reaction of methyl 2-methyl-4-bromo-5-trifluoromethylbenzoate with methylthiozinc chloride in the presence of PD(II)-[1,1'-bis(diphenylphosphino)ferrocene] chloride and CuI, subsequent oxidation with $H_2O_2$, hydrolysis and conversion into the acid chloride, e.g. with $SOCl_2$] with 1.5 g of guanidine in methanol, N-diaminomethylene-2-methyl-4-(methylsulfonyl)-5-trifluoromethylbenzamide is obtained.

The following are obtained analogously by reaction of guanidine with 2-methyl-4-phenylsulfonyl-5-trifluoromethylbenzoyl chloride N-diaminomethylene-2-methyl-4-phenylsulfonyl-5-trifluoromethylbenzamide;
with 2-methyl-4-ethylsulfonyl-5-trifluoromethylbenzoyl chloride N-diaminomethylene-2-methyl-4-ethylsulfonyl-5-trifluoromethylbenzamide;
with 2-methyl-4-propylsulfonyl-5-trifluoromethylbenzoyl chloride N-diaminomethylene-2-methyl-4-propylsulfonyl-5-trifluoromethylbenzamide;
with 2-methyl-4-butylsulfonyl-5-trifluoromethylbenzoyl chloride N-diaminomethylene-2-methyl-4-butylsulfonyl-5-trifluoromethylbenzamide;
with 2-methyl-4-(2-butylsulfonyl)-5-trifluoromethylbenzoyl chloride N-diaminomethylene-2-methyl-4-(2-butylsulfonyl)-5-trifluoromethylbenzamide;
with 2-methyl-4-pentylsulfonyl-5-trifluoromethylbenzoyl chloride N-diaminomethylene-2-methyl-4-pentylsulfonyl-5-trifluoromethylbenzamide;
with 2-methyl-4-(2-pentylsulfonyl)-5-trifluoromethylbenzoyl chloride N-diaminomethylene-2-methyl-4-(2-pentylsulfonyl)-5-trifluoromethylbenzamide;
with 2-methyl-4-(3-pentylsulfonyl)-5-trifluoromethylbenzoyl chloride N-diaminomethylene-2-methyl-4-(3-pentylsulfonyl)-5-trifluoromethylbenzamide;
with 2-methyl-4-tert-butylylsulfonyl-5-trifluoromethylbenzoyl chloride N-diaminomethylene-2-methyl-4-tert-butylsulfonyl-5-trifluoromethylbenzamide;
with 2-methyl-4-isopropylsulfonyl-5-trifluoromethylbenzoyl chloride N-diaminomethylene-2-methyl-4-isopropylsulfonyl-5-trifluoromethylbenzamide;
with 2-methyl-4-hexylsulfonyl-5-trifluoromethylbenzoyl chloride N-diaminomethylene-2-methyl-4-hexylsulfonyl-5-trifluoromethylbenzamide;
with 2-methyl-4-cyclopropylsulfonyl-5-trifluoromethylbenzoyl chloride N-diaminomethylene-2-methyl-4-cyclopropylsulfonyl-5-trifluoromethylbenzamide;
with 2-methyl-4-cyclopentylsulfonyl-5-trifluoromethylbenzoyl chloride N-diaminomethylene-2-methyl-4-cyclopentylsulfonyl-5-trifluoromethylbenzamide;
with 2-methyl-4-cyclohexylsulfonyl-5-trifluoromethylbenzoyl chloride N-diaminomethylene-2-methyl-4-cyclohexylsulfonyl-5-trifluoromethylbenzamide;
with 2-methyl-4-(2-methylcyclopentylsulfonyl)-5trifluoromethylbenzoyl chloride N-diaminomethylene-2-methyl-4-(2-methylcyclopentylsulfonyl)-5-trifluoromethylbenzamide;
with 2-methyl-4-cyclobutylsulfonyl-5-trifluoromethyl benzoyl chloride N-diaminomethylene-2-methyl-4-cyclobutylsulfonyl-5-trifluoromethylbenzamide;
with 2-methyl-4-cycloheptylsulfonyl-5-trifluoromethylbenzoyl chloride N-diaminomethylene-2-methyl-4-cycloheptylsulfonyl-5-trifluoromethylbenzamide;
with 2-ethyl-4-phenylsulfonyl-5-trifluoromethylbenzoyl chloride N-diaminomethylene-2-ethyl-4-phenylsulfonyl-5-trifluoromethylbenzamide;
with 2-ethyl-4,5-di(methylsulfonyl)benzoyl chloride N-diaminomethylene-2-ethyl-4-methylsulfonyl-5-trifluoromethylbenzamide;
with 2-ethyl-4-ethylsulfonyl-5-trifluoromethylbenzoyl chloride N-diaminomethylene-2-ethyl-4-ethylsulfonyl-5-trifluoromethylbenzamide;
with 2-ethyl-4-propylsulfonyl-5-trifluoromethylbenzoyl chloride N-diaminomethylene-2-ethyl-4-propylsulfonyl-5-trifluoromethylbenzamide;
with 2-ethyl-4-butylsulfonyl-5-trifluoromethylbenzoyl chloride N-diaminomethylene-2-ethyl-4-butylsulfonyl-5-trifluoromethylbenzamide;
with 2-ethyl-4-(2-butylsulfonyl)-5-trifluoromethylbenzoyl chloride N-diaminomethylene-2-ethyl-4-(2-butylsulfonyl)-5-trifluoromethylbenzamide;
with 2-ethyl-4-pentylsulfonyl-5-trifluoromethylbenzoyl chloride N-diaminomethylene-2-ethyl-4-pentylsulfonyl-5-trifluoromethylbenzamide;
with 2-ethyl-4-(2-pentylsulfonyl)-5-trifluoromethylbenzoyl chloride N-diaminomethylene-2-ethyl-4-(2-pentysulfonyl)-5-trifluoromethylbenzamide;
with 2-ethyl-4-(3-pentylsulfonyl)-5-trifluoromethylbenzoyl chloride N-diaminomethylene-2-ethyl-4-(3-pentylsulfonyl)-5-trifluoromethylbenzamide;
with 2-ethyl-4-tert-butylsulfonyl-5-trifluoromethylbenzoyl chloride N-diaminomethylene-2-ethyl-4-tert-butylsulfonyl-5-trifluoromethylbenzamide;
with 2-ethyl-4-isopropylsulfonyl-5-trifluoromethylbenzoyl chloride N-diaminomethylene-2-ethyl-4-isopropylsulfonyl-5-trifluoromethylbenzamide;

with 2-ethyl-4-hexylsulfonyl-5-trifluoromethylbenzoyl chloride

N-diaminomethylene-2-ethyl-4-hexylsulfonyl-5-trifluoromethylbenzamide;

with 2-ethyl-4-cyclopropylsulfonyl-5-trifluoromethylbenzoyl chloride

N-diaminomethylene-2-ethyl-4-cyclopropylsulfonyl-5-trifluoromethylbenzamide;

with 2-ethyl-4-cyclopentylsulfonyl-5-trifluoromethylbenzoyl chloride

N-diaminomethylene-2-ethyl-4-cyclopentylsulfonyl-5-trifluoromethylbenzamide;

with 2-ethyl-4-cyclohexylsulfonyl-5-trifluoromethylbenzoyl chloride

N-diaminomethylene-2-ethyl-4-cyclohexylsulfonyl-5-trifluoromethylbenzamide;

with 2-ethyl-4-(2-methylcyclopentylsulfonyl)-5-trifluoromethylbenzoyl chloride

N-diaminomethylene-2-ethyl-4-(2-methylcyclopentylsulfonyl)-5-trifluoromethylbenzamide;

with 2-ethyl-4-cyclobutylsulfonyl-5-trifluoromethylbenzoyl chloride

N-diaminomethylene-2-ethyl-4-cyclobutylsulfonyl-5-trifluoromethylbenzamide;

with 2-ethyl-4-cycloheptylsulfonyl-5-trifluoromethylbenzoyl chloride

N-diaminomethylene-2-ethyl-4-cycloheptylsulfonyl-5-trifluoromethylbenzamide.

Example 4

700 mg of N-diaminomethylene-2-methyl-4,5-di(methylsulfonyl)benzamide [obtainable according to Ex. 1] are suspended in 50 ml of water and treated with 1.8 ml of 1N HCl with stirring. After filtration and lyophilization, N-diaminomethylene-2-methyl-4,5-di(methylsulfonyl)benzamide is obtained; hydrochloride, m.p.>240°.

The following hydrochlorides are obtained analogously from the free bases:

N-diaminomethylene-2-methyl-4-phenylsulfonyl-5-methylsulfonylbenzamide, hydrochloride, m.p. >260°;

N-diaminomethylene-2-methyl-4-cyclopropylsulfonyl-5methylsulfonylbenzamide, hydrochloride;

N-diaminomethylene-2-methyl-4-ethylsulfonyl-5-methylsulfonylbenzamide, hydrochloride;

N-diaminomethylene-2-methyl-4-propylsulfonyl-5-methylsulfonylbenzamide, hydrochloride;

N-diaminomethylene-2-methyl-4-cyclopentylsulfonyl-5-methylsulfonylbenzamide, hydrochloride;

N-diaminomethylene-2-methyl-4-isopropylsulfonyl-5-methylsulfonylbenzamide, hydrochloride;

N-diaminomethylene-2-methyl-4-isopropylsulfonyl-5-nitrobenzamide, hydrochloride;

N-diaminomethylene-2-methyl-4-methylsulfonyl-5-nitrobenzamide, hydrochloride;

N-diaminomethylene-2-methyl-4-methylsulfonyl-5trifluoromethylbenzamide, hydrochloride;

N-diaminomethylene-2-methyl-4-isopropylsulfonyl-5trifluoromethylbenzamide, hydrochloride;

N-diaminomethylene-2-ethyl-4,5-di(methylsulfonyl)benzamide, hydrochloride;

N-diaminomethylene-2-ethyl-4-methylsulfonyl-5-nitrobenzamide, hydrochloride;

N-diaminomethylene-2-ethyl-4-methylsulfonyl-5-trifluoromethylbenzamide, hydrochloride;

N-diaminomethylene-2-ethyl-4-cyclopropylsulfonyl-5-methylsulfonylbenzamide, hydrochloride;

N-diaminomethylene-2-ethyl-4-cyclopentylsulfonyl-5-methylsulfonylbenzamide, hydrochloride;

N-diaminomethylene-2-ethyl-4-butyl-5-methylsulfonylbenzamide, hydrochloride.

Example 5

A suspension of 1 g of N-diaminomethylene-2-methyl-4-chloro-5-methylsulfonylbenzamide [obtainable by reaction of 2-methyl-4-chloro-5-methylsulfonylbenzoyl chloride with guanidine in the presence of triethylamine], 7 ml of thiophenol and 6 g of $K_2CO_3$ is heated at 180° for 90 min. It is dissolved in water and extracted with ethyl acetate, and the extract is evaporated. N-Diaminomethylene-2-methyl-4-(2-methylphenylthio)-5-methylsulfonylbenzamide is obtained, from which, after treatment with 1.5 g of sodium perborate in 30 ml of glacial acetic acid over a period of 2 hours at 60° C. in a water bath, N-diaminomethylene-2-methyl-4-(2-methylphenylsulfonyl)-5methylsulfonylbenzamide is obtained after customary working up.

Example 6

Analogously to Example 5, by oxidation of the corresponding thio compounds, which can also be prepared by reaction of N-diaminomethylene-2-alkyl-4arylthio (or 4-alkylthio)-5-methylsulfonylbenzoyl chloride with guanidine in the presence of base, the following phenyl-substituted N-diaminomethylene-2-alkyl-4-phenylsulfonyl-5-methylsulfonylbenzamides are obtained:

from N-diaminomethylene-2-methyl-4-(3-methylphenylthio)-5-methylsulfonylbenzamide N-diaminomethylene-2-methyl-4-(3-methylphenyl sulfonyl)-5-methylsulfonylbenzamide;

N-diaminomethylene-2-methyl-4-(4-methylphenylthio)-5-methylsulfonylbenzamide

N-diaminomethylene-2-methyl-4-(4-methylphenyl sulfonyl)-5-methylsulfonylbenzamide;

from N-diaminomethylene-2-methyl-4-(2,4-dimethylphenylthio)-5-methylsulfonylbenzamide N-diaminomethylene-2-methyl-4-(2,4-dimethylphenyl sulfonyl)-5-methylsulfonylbenzamide;

from N-diaminomethylene-2-methyl-4-(2-chlorophenylthio)-5-methylsulfonylbenzamide N-diaminomethylene-2-methyl-4-(2-chlorophenyl sulfonyl)-5-methylsulfonylbenzamide;

from N-diaminomethylene-2-methyl-4-(3-chlorophenylthio)-5-methylsulfonylbenzamide N-diaminomethylene-2-methyl-4-(3-chlorophenyl sulfonyl)-5-methylsulfonylbenzamide;

from N-diaminomethylene-2-methyl-4-(4-chlorophenylthio)-5-methylsulfonylbenzamide N-diaminomethylene-2-methyl-4-(4-chlorophenyl sulfonyl)-5-methylsulfonylbenzamide;

from N-diaminomethylene-2-methyl-4-(2-bromophenylthio)-5-methylsulfonylbenzamide N-diaminomethylene-2-methyl-4-(2-bromophenyl sulfonyl)-5-methylsulfonylbenzamide;

from N-diaminomethylene-2-methyl-4-(4-bromophenylthio)-5-methylsulfonylbenzamide N-diaminomethylene-2-methyl-4-(4bromophenylsulfonyl)-5-methylsulfonylbenzamide;

from N-diaminomethylene-2-methyl-4-(2-trifluoromethylphenylthio)-5-methylsulfonylbenzamide N-diaminomethylene-2-methyl-4-(2-trifluoromethyl phenylsulfonyl)-5-methylsulfonylbenzamide;

from N-diaminomethylene-2-methyl-4-(3-trifluoromethylphenylthio)-5-methylsulfonylbenzamide N-diaminomethylene-2-methyl-4-(3-trifluoromethyl phenylsulfonyl)-5-methylsulfonylbenzamide;

from N-diaminomethylene-2-methyl-4-(4-trifluoromethylphenylthio)-5-methylsulfonylbenzamide N-diaminomethylene- 2-methyl-4-(4-trifluoromethylphenylsulfonyl)-5-methylsulfonylbenzamide;

from N-diaminomethylene-2-ethyl-4-(2-methylphenylthio)-5-methylsulfonylbenzamide N-diaminomethylene-2-ethyl-4-(2-methylphenylsulfonyl)-5-methylsulfonylbenzamide;

from N-diaminomethylene-2-ethyl-4-(3-methylphenylthio)-5-methylsulfonylbenzamide N-diaminomethylene-2-ethyl-4-(3-methylphenylsulfonyl)-5-methylsulfonylbenzamide;

from N-diaminomethylene-2-ethyl-4-(4-methylphenylthio)-5-methylsulfonylbenzamide N-diaminomethylene-2-ethyl-4-(4-methylphenylsulfonyl)-5-methylsulfonylbenzamide;

from N-diaminomethylene-2-ethyl-4-(2,4-dimethylphenylthio)-5-methylsulfonylbenzamide N-diaminomethylene-2-ethyl-4-(2,4-dimethylphenylsulfonyl)-5-methylsulfonylbenzamide;

from N-diaminomethylene-2-ethyl-4-(2-chlorophenylthio)-5-methylsulfonylbenzamide N-diaminomethylene-2-ethyl-4-(2-chlorophenylsulfonyl)-5-methylsulfonylbenzamide;

from N-diaminomethylene-2-ethyl-4-(3-chlorophenylthio)-5-methylsulfonylbenzamide N-diaminomethylene-2-ethyl-4-(3-chlorophenylsulfonyl)-5-methylsulfonylbenzamide;

from N-diaminomethylene-2-ethyl-4-(4-chlorophenylthio)-5-methylsulfonylbenzamide N-diaminomethylene-2-ethyl-4-(4-chlorophenylsulfonyl)-5-methylsulfonylbenzamide;

from N-diaminomethylene-2-ethyl-4-(2-bromophenylthio)-5-methylsulfonylbenzamide

N-diaminomethylene-2-ethyl-4-(2-bromophenylsulfonyl)-5-methylsulfonylbenzamide;

from N-diaminomethylene-2-ethyl-4-(4-bromophenylthio)-5-methylsulfonylbenzamide

N-diaminomethylene-2-ethyl-4-(4-bromophenylsulfonyl)-5-methylsulfonylbenzamide;

from N-diaminomethylene-2-ethyl-4-(2-trifluoromethylphenylthio)-5-methylsulfonylbenzamide N-diaminomethylene-2-ethyl-4-(2-trifluoromethyl phenylsulfonyl)-5-methylsulfonylbenzamide;

from N-diaminomethylene-2-ethyl-4-(3-trifluoromethylphenylthio)-5-methylsulfonylbenzamide N-diaminomethylene-2-ethyl-4-(3-trifluoromethyl phenylsulfonyl)-5-methylsulfonylbenzamide;

from N-diaminomethylene-2-ethyl-4-(4-trifluoromethylphenylthio)-5-methylsulfonylbenzamide N-diaminomethylene-2-ethyl-4-(4-trifluoromethyl phenylsulfonyl)-5-methylsulfonylbenzamide.

Example 7

Analogously to Example 1, by reaction of 1.3 g of 2-methyl-4-methylsulfinyl-5-methylsulfonylbenzoyl chloride [obtainable by reaction of 2-methyl-4-chloro-5-methylsulfonylbenzoic acid with Na methanethiolate, subsequent partial oxidation with hydrogen peroxide and conversion into the acid chloride, e.g. with $SOCl_2$] with guanidine, N-diaminomethylene-2-methyl-4-methylsulfinyl-5-methylsulfonylbenzamide is obtained after customary working up and recrystallization from diethyl ether.

The following are obtained analogously by reaction of guanidine with 2-methyl-4-phenylsulfinyl-5-methylsulfonylbenzoyl chloride N-diaminomethylene-2-methyl-4-phenylsulfinyl-5methylsulfonylbenzamide, m.p. 235°–237°;

with 2-methyl-4-ethylsulfinyl-5-methylsulfonylbenzoyl chloride

N-diaminomethylene-2-methyl-4-ethylsulfinyl-5-methylsulfonylbenzamide;

with 2-methyl-4-propylsulfinyl-5-methylsulfonylbenzoyl chloride

N-diaminomethylene-2-methyl-4-propylsulfinyl-5-methylsulfonylbenzamide;

with 2-methyl-4-butylsulfinyl-5-methylsulfonylbenzoyl chloride

N-diaminomethylene-2-methyl-4-butylsulfinyl-5-methylsulfonylbenzamide;

with 2-methyl-4-(2-butylsulfinyl)-5-methylsulfonylbenzoyl chloride

N-diaminomethylene-2-methyl-4-(2-butylsulfinyl)-5-methylsulfonylbenzamide;

with 2-methyl-4-pentylsulfinyl-5-methylsulfonylbenzoyl chloride

N-diaminomethylene-2-methyl-4-pentylsulfinyl-5-methylsulfonylbenzamide;

with 2-methyl-4-(2-pentylsulfinyl)-5-methylsulfonylbenzoyl chloride

N-diaminomethylene-2-methyl-4-(2-pentylsulfinyl)-5-methylsulfonylbenzamide;

with 2-methyl-4-(3-pentylsulfinyl)-5-methylsulfonylbenzoyl chloride

N-diaminomethylene-2-methyl-4-(3-pentylsulfinyl)-5-methylsulfonylbenzamide;

with 2-methyl-4-tert-butylsulfinyl-5-methylsulfonylbenzoyl chloride

N-diaminomethylene-2-methyl-4-tert-butylsulfinyl-5-methylsulfonylbenzamide;

with 2-methyl-4-isopropylsulfinyl-5methylsulfonylbenzoyl chloride

N-diaminomethylene-2-methyl-4-isopropylsulfinyl-5methylsulfonylbenzamide;

with 2-methyl-4-hexylsulfinyl-5-methylsulfonylbenzoyl chloride

N-diaminomethylene-2-methyl-4-hexylsulfinyl-5-methylsulfonylbenzamide;

with 2-methyl-4-cyclopropylsulfinyl-5-methylsulfonylbenzoyl chloride

N-diaminomethylene-2-methyl-4-cyclopropylsulfinyl-5-methylsulfonylbenzamide;

with 2-methyl-4-cyclopentylsulfinyl-5-methylsulfonylbenzoyl chloride

N-diaminomethylene-2-methyl-4-cyclopentylsulfinyl-5-methylsulfonylbenzamide;

with 2-methyl-4-cyclohexylsulfinyl-5-methylsulfonylbenzoyl chloride

N-diaminomethylene-2-methyl-4-cylcohexylsulfinyl-5-methylsulfonylbenzamide;

with 2-methyl-4-(2-methylcyclopentylsulfinyl)-5-methylsulfonylbenzoyl chloride

N-diaminomethylene-2-methyl-4-(2-methylcyclopentylsulfinyl)-5-methylsulfonylbenzamide;

with 2-methyl-4-cyclobutylsulfinyl-5-methylsulfonylbenzoyl chloride

N-diaminomethylene-2-methyl-4-cyclobutylsulfinyl-5-methylsulfonylbenzamide;

with 2-methyl-4-cycloheptylsulfinyl-5-methylsulfonylbenzoyl chloride

N-diaminomethylene-2-methyl-4-cycloheptylsulfinyl-5-methylsulfonylbenzamide;

with 2-ethyl-4-phenylsulfinyl-5-methylsulfonylbenzoyl chloride

N-diaminomethylene-2-ethyl-4-phenylsulfinyl-5-methylsulfonylbenzamide;

with 2-ethyl-4,5-di(methylsulfinyl)benzoyl chloride

N-diaminomethylene-2-ethyl-4,5-di(methylsulfinyl) benzamide;

with 2-ethyl-4-ethylsulfinyl-5-methylsulfonylbenzoyl chloride

N-diaminomethylene-2-ethyl-4-ethylsulfinyl-5-methylsulfonylbenzamide;

with 2-ethyl-4-propylsulfinyl-5-methylsulfonylbenzoyl chloride

N-diaminomethylene-2-ethyl-4-propylsulfinyl-5methylsulfonylbenzamide;

with 2-ethyl-4-butylsulfinyl-5-methylsulfonylbenzoyl chloride

N-diaminomethylene-2-ethyl-4-butylsulfinyl-5-methylsulfonylbenzamide;

with 2-ethyl-4-(2-butylsulfinyl)-5-methylsulfonylbenzoyl chloride

N-diaminomethylene-2-ethyl-4-(2-butylsulfinyl)-5-methylsulfonylbenzamide;

with 2-ethyl-4-pentylsulfinyl-5-methylsulfonylbenzoyl chloride

N-diaminomethylene-2-ethyl-4-pentylsulfinyl-5-methylsulfonylbenzamide;

with 2-ethyl-4-(2-pentylsulfinyl)-5-methylsulfonylbenzoyl chloride

N-diaminomethylene-2-ethyl-4-(2-pentylsulfinyl)-5-methylbenzamide;

with 2-ethyl-4-(3-pentylsulfinyl)-5-methylsulfonylbenzoyl chloride

N-diaminomethylene-2-ethyl-4-(3-pentylsulfinyl)-5-methylsulfonylbenzamide;

with 2-ethyl-4-tert-butylsulfinyl-5-methylsulfonylbenzoyl chloride

N-diaminomethylene-2-ethyl-4-tert-butylsulfinyl-5-methylsulfonylbenzamide;

with 2-ethyl-4-isopropylsulfinyl-5-methylsulfonylbenzoyl chloride

N-diaminomethylene-2-ethyl-4-isopropylsulfinyl-5-methylsulfonylbenzamide;

with 2-ethyl-4-hexylsulfinyl-5-methylsulfonylbenzoyl chloride

N-diaminomethylene-2-ethyl-4-hexylsulfinyl-5-methylsulfonylbenzamide;

with 2-ethyl-4-cyclopropylsulfinyl-5-methylsulfonylbenzoyl chloride

N-diaminomethylene-2-ethyl-4-cyclopropylsulfinyl-5-methylsulfonylbenzamide;

with 2-ethyl-4-cyclopentylsulfinyl-5-methylsulfonylbenzoyl chloride

N-diaminomethylene-2-ethyl-4-cyclopentylsulfinyl-5-methylsulfonylbenzamide;

with 2-ethyl-4-cyclohexylsulfinyl-5-methylsulfonylbenzoyl chloride

N-diaminomethylene-2-ethyl-4-cyclohexylsulfinyl-5-methylsulfonylbenzamide;

with 2-ethyl-4-(2-methylcyclopentylsulfinyl)-5-methylsulfonylbenzoyl chloride

N-diaminomethylene-2-ethyl-4-(2-methylcyclopentyl sulfinyl)-5-methylsulfonylbenzamide;

with 2-ethyl-4-cyclobutylsulfinyl-5-methylsulfonylbenzoyl chloride

N-diaminomethylene-2-ethyl-4-cyclobutylsulfinyl-5-methylsulfonylbenzamide;

with 2-ethyl-4-cycloheptylsulfinyl-5-methylsulfonylbenzoyl chloride

N-diaminomethylene-2-ethyl-4-cycloheptylsulfinyl-5-methylsulfonylbenzamide.

Example 8

To a suspension of 1 g of N-diaminomethylene-2-methyl-4-bromo-5-nitrobenzamide [obtainable by reaction of 2-methyl-4-bromo-5-methylsulfonylbenzoyl chloride with guanidine in the presence of triethylamine] in 70 ml of THF are added successively 20 mg of Pd(II)-[1,1'-bis (diphenylphosphine)ferrocene]chloride, 10 mg of CuI and 2 equivalents of phenylsulfinylzinc chloride, dissolved in 10 ml of THF, and the mixture is stirred at room temperature for 2 hours. After filtration, removal of the solvent and customary working up, N-diaminomethylene-2-methyl-4-phenylsulfinyl-5-nitrobenzamide is then obtained, from which the corresponding hydrochloride is obtained after treatment with diluted aqueous Cl solution and freeze-drying.

Example 9

Analogously to Example 6, by oxidation of the corresponding thio compounds, which can be prepared as described before, by reaction with 2-alkyl-4-arylthio-5-nitrobenzoyl chloride with guanidine in the presence of base, the following aryl-substituted N-diaminomethylene-2-alkyl-4-arylsulfonyl-5-nitrobenzamides are obtained:

from N-diaminomethylene-2-methyl-4-(3-methylphenylthio)-5-nitrobenzamide

N-diaminomethylene-2-methyl-4-(3-methylphenylsulfonyl)-5-nitrobenzamide;

from N-diaminomethylene -2-methyl-4-(4-methylphenylthio)-5-nitrobenzamide

N-diaminomethylene -2-methyl-4-(4-methylphenylsulfonyl)-5-nitrobenzamide;

from N-diaminomethylene-2-methyl-4-(2,4-dimethylphenylthio)-5-nitrobenzamide

N-diaminomethylene-2-methyl-4-(2,4-dimethylphenylsulfonyl)-5-nitrobenzamide;

from N-diaminomethylene-2-methyl-4-(2-chlorophenylthio)-5-nitrobenzamide

N-diaminomethylene-2-methyl-4-(2-chlorophenylsulfonyl)-5-nitrobenzamide;

from N-diaminomethylene-2-methyl-4-(3-chlorophenylthio)-5-nitrobenzamide

N-diaminomethylene-2-methyl-4-(3-chlorophenylsulfonyl)-5-nitrobenzamide;

from N-diaminomethylene-2-methyl-4-(4-chlorophenylthio)-5-nitrobenzamide

N-diaminomethylene-2-methyl-4-(4-chlorophenylsulfonyl)-5-nitrobenzamide;
from N-diaminomethylene-2-methyl-4-(2-bromophenylthio)-5-nitrobenzamide N-diaminomethylene-2-methyl-4-(2-bromophenylsulfonyl)-5-nitrobenzamide;
from N-diaminomethylene-2-methyl-4-(4-bromophenylthio)-5-nitrobenzamide N-diaminomethylene-2-methyl-4-(4-bromophenylsulfonyl)-5-nitrobenzamide;
from N-diaminomethylene-2-methyl-4-(2-trifluoromethylphenylthio)-5-nitrobenzamide N-diaminomethylene-2-methyl-4-(2-trifluoromethylphenylsulfonyl)-5-nitrobenzamide;
from N-diaminomethylene-2-methyl-4-(3-trifluoromethylphenylthio)-5-nitrobenzamide N-diaminomethylene-2-methyl-4-(3-trifluoromethylphenylsulfonyl)-5-nitrobenzamide;
from N-diaminomethylene-2-methyl-4-(4-trifluoromethylphenylthio)-5-nitrobenzamide N-diaminomethylene -2-methyl-4-(4-trifluoromethylphenylsulfonyl)-5-nitrobenzamide;
from N-diaminomethylene-2-ethyl-4-(2-methylphenylthio)-5-nitrobenzamide N-diaminomethylene-2-ethyl-4-(2-methylphenylsulfonyl)-5-nitrobenzamide;
from N-diaminomethylene-2-ethyl-4-(3-methylphenylthio)-5-nitrobenzamide N-diaminomethylene-2-ethyl-4-(3-methylphenylsulfonyl)-5-nitrobenzamide;
from N-diaminomethylene-2-ethyl-4-(4-methylphenylthio)-5-nitrobenzamide N-diaminomethylene-2-ethyl-4-(4-methylphenylsulfonyl)-5-nitrobenzamide;
from N-diaminomethylene-2-ethyl-4-(2,4-dimethylphenylthio)-5-nitrobenzamide N-diaminomethylene-2-ethyl-4-(2,4-dimethylphenylsulfonyl)-5-nitrobenzamide;
from N-diaminomethylene-2-ethyl-4-(2-chlorophenylthio)-5-nitrobenzamide N-diaminomethylene-2-ethyl-4-(2-chlorophenylsulfonyl)-5-nitrobenzamide;
from N-diaminomethylene-2-ethyl-4-(3-chlorophenylthio)-5-nitrobenzamide N-diaminomethylene-2-ethyl-4-(3-chlorophenylsulfonyl)-5-nitrobenzamide;
from N-diaminomethylene-2-ethyl-4-(4-chlorophenylthio)-5-nitrobenzamide N-diaminomethylene-2-ethyl-4-(4-chlorophenylsulfonyl)-5-nitrobenzamide;
from N-diaminomethylene-2-ethyl-4-(2-bromophenylthio)-5-nitrobenzamide N-diaminomethylene-2-ethyl-4-(2-bromophenylsulfonyl)-5-nitrobenzamide;
from N-diaminomethylene-2-ethyl-4-(4-bromophenylthio)-5-nitrobenzamide N-diaminomethylene-2-ethyl-4-(4-bromophenylsulfonyl)-5-nitrobenzamide;
from N-diaminomethylene-2-ethyl-4-(2-trifluoromethylphenylthio)-5-nitrobenzamide N-diaminomethylene-2-ethyl-4-(2-trifluoromethylphenylsulfonyl)-5-nitrobenzamide;
from N-diaminomethylene-2-ethyl-4-(3-trifluoromethylphenylthio)-5-nitrobenzamide N-diaminomethylene-2-ethyl-4-(3-trifluoromethylphenylsulfonyl)-5-nitrobenzamide;
from N-diaminomethylene-2-ethyl-4-(4-trifluoromethylphenylthio)-5-nitrobenzamide N-diaminomethylene-2-ethyl-4-(4-trifluoromethylphenylsulfonyl)-5-nitrobenzamide.

Example 10

Analogously to Example 6, by oxidation of the corresponding thio compounds, which can be prepared as described before, by reaction of 2-alkyl-4-arylthio-5-trifluoromethylbenzoyl chloride with guanidine in the presence of base, the following phenyl-substituted N-diaminomethylene-2-alkyl-4-phenylsulfonyl-5-trifluoromethylbenzamides are obtained:
from N-diaminomethylene-2-methyl-4-(3-methylphenylthio)-5-trifluoromethylbenzamide N-diaminomethylene-2-methyl-4-(B-methylphenylsulfonyl)-5-trifluoromethylbenzamide;
from N-diaminomethylene-2-methyl-4-(4-methylphenylthio)-5-trifluoromethylbenzamide N-diaminomethylene-2-methyl-4-(4-methylphenylsulfonyl)-5-trifluoromethylbenzamide; from N-diaminomethylene-2-methyl-4-(2,4-dimethylphenylthio)-5-trifluoromethylbenzamide N-diaminomethylene-2-methyl-4-(2, 4-dimethylphenylsulfonyl)-5-trifluoromethylbenzamide;
from N-diaminomethylene-2-methyl-4-(2-chlorophenylthio)-5-trifluoromethylbenzamide N-diaminomethylene-2-methyl-4-(2-chlorophenylsulfonyl)-5-trifluoromethylbenzamide;
from N-diaminomethylene-2-methyl-4-(3-chlorophenylthio)-5-trifluoromethylbenzamide N-diaminomethylene-2-methyl-4-(3-chlorophenylsulfonyl)-5-trifluoromethylbenzamide;
from N-diaminomethylene-2-methyl-4-(4-chlorophenylthio)-5-trifluoromethylbenzamide N-diaminomethylene-2-methyl-4-(4-chlorophenylsulfonyl)-5-trifluoromethylbenzamide;
from N-diaminomethylene-2-methyl-4-(2-bromophenylthio)-5-trifluoromethylbenzamide N-diaminomethylene-2-methyl-4-(2-bromophenylsulfonyl)-5-trifluoromethylbenzamide;
from N-diaminomethylene-2-methyl-4-(4-bromophenylthio)-5-trifluoromethylbenzamide N-diaminomethylene-2-methyl-4-(4-bromophenylsulfonyl)-5-trifluoromethylbenzamide;
from N-diaminomethylene-2-methyl-4-(2-trifluoromethylphenylthio)-5-trifluoromethylbenzamide N-diaminomethylene-2-methyl-4-(2-trifluoromethylphenylsulfonyl)-5-trifluoromethylbenzamide;
from N-diaminomethylene-2-methyl-4-(3-trifluoromethylphenylthio)-5-trifluoromethylbenzamide N-diaminomethylene-2-methyl-4-(3-trifluoromethylphenylsulfonyl)-5-trifluoromethylbenzamide;
from N-diaminomethylene-2-methyl-4-(4-trifluoromethylphenylthio)-5-trifluoromethylbenzamide N-diaminomethylene-2-methyl-4-(4-trifluoromethylphenylsulfonyl)-5-trifluoromethylbenzamide;
from N-diaminomethylene-2-ethyl-4-(2-methylphenylthio)-5-trifluoromethylbenzamide N-diaminomethylene-2-ethyl-4-(2-methylphenylsulfonyl)-5-trifluoromethylbenzamide;

from N-diaminomethylene-2-ethyl-4-(3-methylphenylthio)-5-trifluoromethylbenzamide N-diaminomethylene-2-ethyl-4-(3-methylphenylsulfonyl)-5-trifluoromethylbenzamide;
from N-diaminomethylene-2-ethyl-4-(4-methylphenylthio)-5-trifluoromethylbenzamide N-diaminomethylene-2-ethyl-4-(4-methylphenylsulfonyl)-5-trifluoromethylbenzamide;
from N-diaminomethylene-2-ethyl-4-(2,4-dimethylphenylthio)-5-trifluoromethylbenzamide N-diaminomethylene-2-ethyl-4-(2,4-dimethylphenylsulfonyl)-5-trifluoromethylbenzamide;
from N-diaminomethylene-2-ethyl-4-(2-chlorophenylthio)-5-trifluoromethylbenzamide N-diaminomethylene-2-ethyl-4-(2-chlorophenylsulfonyl)-5-trifluoromethylbenzamide;
from N-diaminomethylene-2-ethyl-4-(3-chlorophenylthio)-5-trifluoromethylbenzamide N-diaminomethylene-2-ethyl-4-(3-chlorophenylsulfonyl)-5-trifluoromethylbenzamide;
from N-diaminomethylene-2-ethyl-4-(4-chlorophenylthio)-5-trifluoromethylbenzamide N-diaminomethylene-2-ethyl-4-(4-chlorophenylsulfonyl)-5-trifluoromethylbenzamide;
from N-diaminomethylene-2-ethyl-4-(2-bromophenylthio)-5-trifluoromethylbenzamide N-diaminomethylene-2-ethyl-4-(2-bromophenylsulfonyl)-5-trifluoromethylbenzamide;
from N-diaminomethylene-2-ethyl-4-(4-bromophenylthio)-5-trifluoromethylbenzamide N-diaminomethylene-2-ethyl-4-(4-bromophenylsulfonyl)-5-trifluoromethylbenzamide;
from N-diaminomethylene-2-ethyl-4-(2-trifluoromethylphenylthio)-5-trifluoromethylbenzamide N-diaminomethylene-2-ethyl-4-(2-trifluoromethylphenylsulfonyl)-5-trifluoromethylbenzamide;
from N-diaminomethylene-2-ethyl-4-(3-trifluoromethylphenylthio)-5-trifluoromethylbenzamide N-diaminomethylene-2-ethyl-4-(3-trifluoromethylphenylsulfonyl)-5-trifluoromethylbenzamide;
from N-diaminomethylene-2-ethyl-4-(4-trifluoromethylphenylthio)-5-trifluoromethylbenzamide N-diaminomethylene-2-ethyl-4-(4-trifluoromethylphenylsulfonyl)-5-trifluoromethylbenzamide.

The following examples relate to pharmaceutical preparations:

Example A: Injection vials

A solution of 100 g of an active compound of the formula I and 5 g of disodium hydrogen phosphate is adjusted to pH 6.5 in 3 l of double-distilled water using 2 N hydrochloric acid, sterile-filtered, dispensed into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into molds and allowed to cool. Each suppository contains 20 mg of active compound.

Example C: Solution

A solution is prepared from 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. It is adjusted to pH 6.8, made up to 1 l and sterilized by irradiation. This solution can be used in the form of eye drops.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed to give tablets in a customary manner in such a way that each tablet contains 10 mg of active compound.

Example F: Coated tablets

Analogously to Example E, tablets are pressed which are then coated in a customary manner with a coating of sucrose, potato starch, talc, tragacanth and colorant.

Example G: Capsules 2 kg of active compound of the formula I are dispensed into hard gelatin capsules in a customary manner such that each capsule contains 20 mg of the active compound.

Example H: Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A 4- sulfonyl- or 4-sulfinylbenzoylguanidine compound of formula I

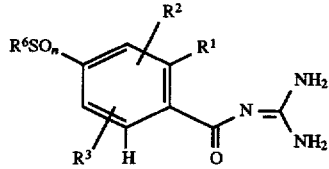

wherein $R^1$ is A, $CF_3$, $CH_2F$, $CHF_2$, $C_2F_5$, CN, $NO_2$ or Hal, $R^2$ is $-SO_n-R^6$, $-SO_2NR^4R^5$, $NO_2$ or $CF_3$, $R^3$ is H, Hal, A, OH, OA, CN, $NO_2$, $CF_3$, $CH_2F$, $CHF_2$, $C_2F_5$ or $CH_2CF_3$, $R^4$ and $R^5$ are each independently, H, A, $C_{5-7}$-cycloalkyl, $C_{4-8}$-cycloalkylmethyl, Ph or $-CH_2-Ph$, or $R^4$ and $R^5$ together are $C_{4-6}$-alkylene wherein a $CH_2$ group is optionally replaced by O, S, NH, N—A or N—$CH_2$-Ph, $R^6$ is A, Ph, Het or $C_{3-7}$-cycloalkyl, Het is a mono- or binuclear saturated, unsaturated or aromatic heterocycle having 1 to 4 N, O and/or S atoms, bonded via N or C, unsubstituted or mono-, di- or trisubstituted by Hal, SH, SA, $NH_2$, NHA, $NA_2$, $CF_3$, A, OH, OA, CN, $NO_2$, NHA, $NA_2$ and/or carbonyl oxygen, A is $C_{1-6}$-alkyl, Hal is F, Cl, Br or I, Ph is phenyl, unsubstituted or mono-, di- or trisubstituted by A, OA, $NR^4R^5$, F, Cl, Br, I or $CF_3$ and n is 1 or 2, or a physiologically acceptable salt thereof.

2. A compound of claim 1, selected from:

(a) N-diaminomethylene-2-methyl-4,5-di(methylsulfonyl)benzamide;

(b) N-diaminomethylene-2-methyl-4-phenylsulfonyl-5-methylsulfonylbenzamide;

(c) N-diaminomethylene-2-methyl-4-tert-butylsulfonyl-5-methylsulfonylbenzamide;

(d) N-diaminomethylene-2-ethyl-4,5-di(methylsulfonyl)benzamide;

(e) N-diaminomethylene-2-ethyl-4-cyclopentylsulfonylbenzamide;

(f) N-diaminomethylene-2-methyl-4-cyclohexylsulfonyl-5-methylsulfonylbenzamide; and (g) N-diaminomethylene-2-methyl-4-methylsulfonyl-5-p-chlorophenylsulfonylbenzamide or a physiologically acceptable salt thereof.

3. A process for the preparation of an alkylbenzoylguanidine compound of formula I of claim 1, or a salt thereof, comprising (a) reacting a compound of formula II

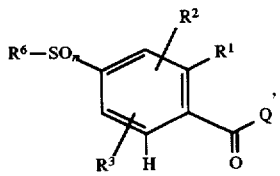

wherein $R^1$, $R^2$, $R^3$, $R^6$, and n have the indicated meanings and Q is Cl, Br, OA, O—CO—A, O—CO—Ph, OH or another reactive esterified OH group or readily nucleophilically substitutable leaving group, with guanidine, or (b) reacting a benzoylguanidine of formula III

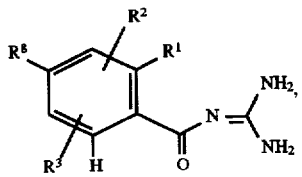

wherein $R^1$ $R^2$ and $R^3$ have the indicated meanings, and $R^8$ is F, Cl, Br, I or H, with a hydrocarbon compound of formula IV

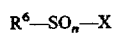

wherein $R^6$ has the indicated meaning and

X is H, Cl, Br or I in the presence of a catalyst, after prior metallation or transmetallation, or (c) reacting a benzoylguanidine of formula V

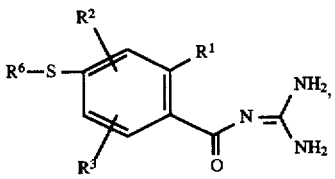

with a suitable oxidizing agent, or (d) treating a compound corresponding to formula I, wherein one or more hydrogen atoms is replaced by one or more reducible groups and/or one or more additional C—C and/or C—N bonds, with a reducing agent, or (e) treating a compound corresponding to formula I, wherein one or more hydrogen atoms is replaced by one or more solvolyzable groups, with a solvolyzing agent and/or (f) converting a base of formula I to a salt thereof by treating with an acid.

4. A pharmaceutical preparation, comprising an effective amount of a compound of formula I of claim 1, or a physiologically acceptable salt thereof and a pharmaceutically acceptable excipient or auxiliary.

5. A method of treating cardiac arrhythmia, angina pectoris or infarction, comprising administering to a patient in need of such treatment a compound of formula I of claim 1, or a pharmaceutically acceptable salt thereof.

6. A method of preventing cardiac arrhythmia, angina pectoris or infarction, comprising administering to a patient in need of such treatment an effective amount of a compound of Formula I of claim 1, or a pharmaceutically acceptable salt thereof.

7. A method of treating hypoxia or ischaemia, comprising administering to a patient in need of such treatment an effective amount of a compound of Formula I of claim 1, or a pharmaceutically acceptable salt thereof.

8. A method of preventing damage caused by hypoxia or ischaemia in organs temporarily undersupplied with oxygen during surgery or organ transplantation, comprising treating such organs with a compound of Formula I of claim 1, or a pharmaceutically acceptable salt thereof.

9. A method of claim 7, wherein the hypoxia or ischaemia is caused by angioplastic vascular or cardiac intervention, ischaemia of the nervous system, or shock.

10. A method of preventing essential hypertension, comprising administering to a patient in need of such treatment an effective amount of a compound of Formula I of claim 1, or a pharmaceutically acceptable salt thereof.

11. A compound of claim 1, wherein in Ia $R^1$ is A and $R^2$ is —$SO_2$—A or $NO_2$;

in Ib $R^1$ is A and $R^6$ is branched or unbranched $C_{1-6}$-alkyl;

in Ic $R^1$ is A and $R^6$ is $C_{5-7}$-cycloalkyl;

in Id $R^6$ is branched or unbranched $C_{1-6}$-alkyl, $R^2$ is —$SO_2$—A, $CF_3$ or $NO_2$ and $R^1$ is methyl or ethyl;

in Ie $R^6$ is methyl, ethyl, propyl, isopropyl, butyl, $C_{3-7}$-cycloalkyl, or phenyl, unsubstituted or monosubstituted by Cl, Br, methyl or $CF_3$, and $R^2$ is in the meta-position relative to the amide group and is —$SO_2$—A;

in If $R^1$ and $R^2$ are in the para-position to one another and $R^1$ is A and $R^2$ is —$SO_2$—A;

in Ig R6 is phenyl or methyl, n is 2, $R^1$ is methyl or ethyl and $R^2$ is in the meta-position relative to the amide group and is —$SO_2$—A;

in Ih $R^1$ is methyl or ethyl, $R^2$ is $SO_2$—$CH_3$ and $R^6$ is methyl, ethyl, propyl, isopropyl, phenyl, cyclopentyl or cyclohexyl.

12. A compound of claim 11, wherein n is 2.

13. A method of treating a disease or condition which is associated with $Na^+/H^+$ antiporter, and treatable by the inhibition thereof, comprising administering to a patient in need of such treatment, an effective amount of a compound of Formula I of claim 1, or a pharmaceutically acceptable salt thereof.

14. A compound of claim 1, wherein n is 1 and is a substantially pure enantiomer.

15. A compound of claim 14, which is the R enantiomer.

16. A compound of claim 14, which is the S enantiomer.

17. The method of claim 5, wherein the alkylbenzoylguanidine is administered in a daily dose of 0.0001–0.1 mg/kg of body weight.

18. The method of claim 7, wherein the compound of the formula I is administered in a daily dose of 0.0001–0.1 mg/kg of body weight.

19. The method of claim 10, wherein the compound of formula I is administered in a daily dose of 0.0001–0.1 mg/kg of body weight.

20. The method of claim 13, wherein the compound of formula I is administered in a daily dose of 0.0001–0.1 mg/kg of body weight.

* * * * *